(12) United States Patent
Frank

(10) Patent No.: US 7,470,278 B2
(45) Date of Patent: Dec. 30, 2008

(54) MEDICAL GRIPPING AND/OR RETAINING INSTRUMENT

(75) Inventor: Timothy Graham Frank, Fife (GB)

(73) Assignee: Karl Storz GmbH & Co. KG (DE)

( * ) Notice: Subject to any disclaimer, the term of this patent is extended or adjusted under 35 U.S.C. 154(b) by 345 days.

(21) Appl. No.: 11/037,310

(22) Filed: Jan. 18, 2005

(65) Prior Publication Data

US 2005/0182442 A1     Aug. 18, 2005

Related U.S. Application Data

(63) Continuation of application No. PCT/EP03/07525, filed on Jul. 11, 2003.

(30) Foreign Application Priority Data

Jul. 16, 2002    (DE) ................................ 102 32 061

(51) Int. Cl.
     *A61B 17/28*      (2006.01)
(52) U.S. Cl. ..................................................... 606/208
(58) Field of Classification Search ................. 606/205, 606/207, 208, 210, 147; 403/157; 81/418, 81/424.5, 426, 367, 368
See application file for complete search history.

(56) References Cited

U.S. PATENT DOCUMENTS

| | | | |
|---|---|---|---|
| 348,537 A | 8/1886 | Stohlmann | |
| 905,007 A | 11/1908 | Sether | |
| 2,150,496 A * | 3/1939 | Ericsson | 606/147 |
| 2,679,779 A | 6/1954 | Spikings | 81/84 |
| 2,743,726 A * | 5/1956 | Grieshaber | 606/207 |
| 2,930,376 A | 3/1960 | Rathmann | 128/305 |
| 3,306,143 A * | 2/1967 | Ortman | 81/368 |
| 3,709,226 A | 1/1973 | Santos | 128/340 |
| 4,139,245 A * | 2/1979 | McCloskey | 384/203 |
| 4,724,838 A | 2/1988 | Hasson | 128/321 |
| 4,776,533 A * | 10/1988 | Sheek et al. | 244/118.6 |
| 5,304,185 A | 4/1994 | Taylor | 606/147 |
| 5,944,718 A | 8/1999 | Austin et al. | 606/48 |
| 6,386,076 B1 | 5/2002 | Swanstrom, Jr. | 81/423 |

FOREIGN PATENT DOCUMENTS

| | | |
|---|---|---|
| DE | 44 12 171 A1 | 10/1995 |
| DE | 690 24 396 T2 | 8/1996 |
| GB | 477 199 | 12/1937 |
| GB | 805 066 | 11/1958 |

\* cited by examiner

*Primary Examiner*—Todd E Manahan
*Assistant Examiner*—Ryan Severson
(74) *Attorney, Agent, or Firm*—St. Onge Steward Johnston & Reens LLC

(57) ABSTRACT

The invention relates to a medical gripping and/or retaining instrument, in particular a needle holder, with a handle consisting of at least two handgrips and a retaining part that consists of at least two jaw members and can be activated by the handle. To create a gripping and/or retaining instrument which ensures that at least one part of a jaw member of the retaining part is mounted so that it can rotate with respect to at least another jaw member working with this jaw member around the longitudinal axis of the jaw member and/or can be displaced in the direction of the longitudinal axis of the jaw member.

9 Claims, 4 Drawing Sheets

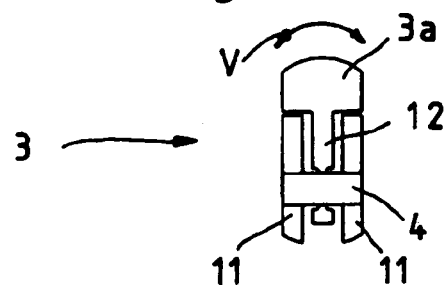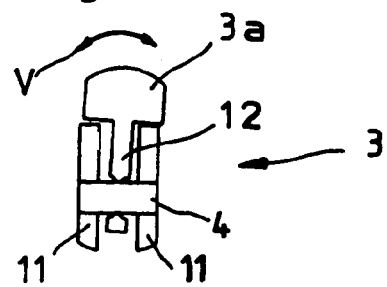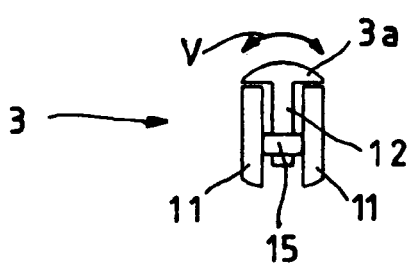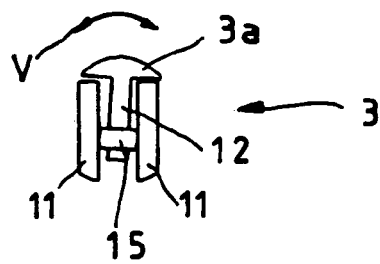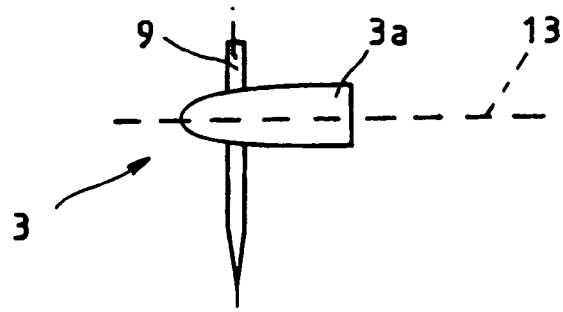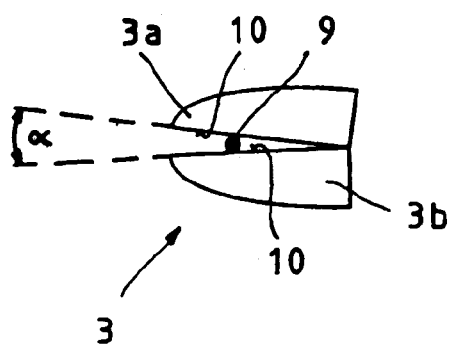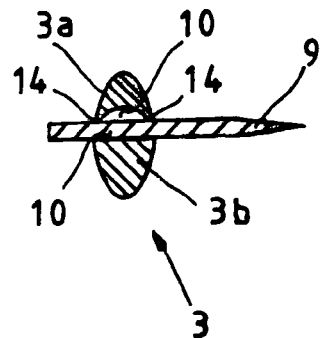

MEDICAL GRIPPING AND/OR RETAINING INSTRUMENT

This application is a continuation of pending International Patent Application No. PCT/EP2003/007525 filed on Jul. 11, 2003 which designates the United States and claims priority of German Patent Application No. 102 32 061.6 filed on Jul. 16, 2002.

FIELD OF THE INVENTION

The invention relates to a medical gripping and/or retaining instrument, in particular a needle holder, with a handle consisting of at least two handgrips and a retaining part that consists of at least two jaw members and can be activated by the handle.

Medical gripping and/or retaining instruments are employed in the widest range of applications, for instance as pincers or needle holders. This familiar gripping and/or retaining instruments are for the most part pincer-shaped and include two gear arms that can rotate around a common swivel axis and whose distal ends form the jaw members of the retaining part, while their proximal ends serve as the handle's handgrips. Because the rotatable jaw members are mounted around a common swivel axis, an opening angle is formed between the opening and closing jaw members, and around it the internal gripping surfaces of the jaw members are mounted, opposite one another, on the rotation axis in relation to the instrument's longitudinal axis. This jaw-type opening angle remains in existence when an object is positioned in the retaining position, clamped between the gripping surfaces of the jaw members.

If the object to be held has a rigid, essentially cylindrical shaft, as is the case with a needle that is to be held by a needle holder, the object can be held between the jaw members so that it resists rotation, only if the object to be held is positioned at a right angle to the instrument's longitudinal axis, because only this angle position allows a linear contact between a gripping surface of a jaw member and the object.

As soon as the object is not positioned between the jaw members at a right angle to the instrument's longitudinal axis, the opening angle formed between the jaw members causes the closing jaw members to hold the object clamped exclusively with the areas of the gripping surfaces situated closest to the swivel axis, so that only a punctual contact is possible between the gripping surfaces and the object. This merely punctual placement of the object between the jaw members is highly unstable, and consequently an object held in such manner rotates with respect to the instrument's longitudinal axis at the slightest pressure. Such rotation is not tolerable for a needle gripped and controlled by a needle holder.

Therefore it is the aim of the invention to design a medical gripping and/or retaining instrument of the aforementioned type in such a manner that an object gripped by the jaw members is held secure against rotation by the jaw members, independently of the object's angle position with respect to the instrument's longitudinal axis.

This aim is fulfilled by the invention through the fact that at least one part of the jaw member of the retaining part is positioned with respect to the at least one other jaw member that works with this jaw member, so that it can rotate around the longitudinal axis of the jaw member and/or can be displaced in the direction of the longitudinal axis of the jaw member.

Because of the rotatable positioning of the at least one jaw member, it is possible for the first time, thanks to the inventions' designed gripping and/or retaining instrument, to hold an object gripped by the jaw members in any desired angle position so that it cannot change position and is secure, because thanks to the rotatability it is possible to configure the opening angle of the jaw members diagonally to the jaw members.

The object to be held by the jaw members can be positioned securely against rotation if the gripping surfaces of the jaw members are contacting the object held between the jaw members of the retaining part, regardless of the object's angle position with respect to the instrument's longitudinal axis, in such a way that these gripping surfaces each contact the object on at least two contact points at a distance from one another. This manner of gripping the object at two contact points per jaw member increases the friction resistance and prevents the formation of a rotation point such as is found when there is merely one punctual contact point.

In a preferred embodiment of the invention, at least one gripping surface of a jaw member contacts the object in an essentially linear manner. Linear contact thus constitutes the most reliable positioning of the object, if the object is cylindrical in shape.

To be able to hold objects securely and firmly between the jaw members that do not have a fixed outer diameter, it is proposed with this invention that the gripping surface of one jaw member has a level configuration and that the gripping surface of another jaw member, working together with the first jaw member, has a vaulted configuration in the longitudinal direction of this first jaw member, facing away from the contact surface with the object to be held, so that the jaw member with the vaulted gripping surface grips the object to be held only with its outer edge and produces two contact points that are secure against rotation and at a distance form one another.

In a practical embodiment of the invention it is proposed that one handgrip of the handle forms a single unit with one jaw member of the retaining part, while the other handgrip of the handle is rotatably connected with the other jaw member of the retaining part, and that the handgrips are connected to one another by at least one guide element, in particular a spring element, in such a way that the guide element is mounted with one end on a mounting point in the area of the proximal end of the one handgrip and with the other end on a mounting point in the middle area of the other handgrip.

To make it possible, despite the rotatable mounting of the jaw member, that the handgrip of the handle connected with this jaw member can be moved up and down to open and close the jaw members without lateral tipping motion, it is further proposed that the rotatable handgrip or the rotatable jaw member is mounted on the hinge axis of the hinge point so that it can tip with respect to the respective other component. Positioning the handgrip so that it can be tipped between the handgrip and the jaw member, together with the guide element positioned between the handgrips, allows a stable tip-proof motion of the handgrip of the handle, because the position in the area of the hinge point again compensates for the possible turning of the jaw member.

According to a first embodiment of the invention, to produce the position that allows at least one part of a jaw member to rotate around the longitudinal axis of the jaw member, this jaw member is of multipartite construction so that it consists of an essentially rigid part and a part that is mounted on the rigid part and can rotate around the longitudinal axis of the rigid part. This embodiment is distinguished in that it is not the entire jaw member that is rotatably positioned, but only a portion that includes the gripping surface. This configuration, moreover, does not have the problem that the rotating in the area of the jaw member causes a rotation/tipping of the handgrip.

To ensure that the jaw member equipped with the rotatable part can be put into operation quickly and simply, the rotation angle of the preferably rotatable part is limited and the rotatable part is pre-stressed by a spring element into a starting position.

In addition, with this embodiment of the invention it is proposed that the rotatable part in the longitudinal direction of the rigid part is mounted so that it can be fixed onto the rigid part.

In a preferred embodiment of the invention, the gripping and/or retaining instrument has a retaining part made up of two jaw members that can rotate around a common swivel axis, and the one jaw member, for receiving the swivel axis, has two parallel side walls at a distance from one another and the other jaw member is mounted on the swivel axis by means of a stud between the two parallel side walls and at a distance from the two side walls.

To make the one jaw member capable of tipping with respect to the other jaw member, it is proposed that the stud that forms the hub in the area resting on the swivel axis is configured in such a way that the bore hole in the stud corresponding to the hub tapers from both sides to the middle of the bore hole all the way to the outer diameter of the swivel axis, so that the second jaw member is preferably mounted in linear manner on a surrounding circular track on the swivel axis.

It is further proposed with this invention that—with an inventive instrument in which one part of a jaw member of the retaining part is positioned so that it can rotate, with respect to at least one other jaw member that works with this jaw member, exclusively around the longitudinal axis of the jaw member—in the stud of the one jaw member a rod is secured which runs perpendicular to the instrument's longitudinal axis and is positioned in the side walls of the other jaw member. This rod, which preferably is positioned in the side walls around the instrument's longitudinal axis, so that it can be tipped, is intended to prevent relative motion of the tippable jaw member in the longitudinal direction of the other jaw member.

It is finally proposed with the invention, alternatively, to achieve movable placement of the jaw member in the direction of the longitudinal axis of the jaw member, that this jaw member is positioned on the other jaw member in such a way that the gripping surfaces of the jaw members move essentially parallel to one another during the opening and closing of the jaw members. This parallel motion is accomplished, according to the invention, in that the jaw members are connected by means of a parallelogram rod structure.

Additional characteristics and advantages can be seen with reference to the following description of the related drawings, in which three embodiments of an inventive medical gripping and/or retaining instrument are presented only in schematic form.

BRIEF DESCRIPTION OF THE DRAWINGS

FIG. 2a shows a section along the section line II-II, with the jaw members in straight position.

FIG. 2b shows a section along the section line II-II, with the jaw members in tipped position.

FIG. 3a shows a section along the section line III-III, with the jaw members in straight position.

FIG. 3b shows a section along the section line III-III, with the jaw members in tipped position.

FIG. 4a shows a schematic overhead view of a retaining part of an inventive gripping and/or retaining instrument with a needle held between the jaw members at a right angle to the instrument's axis.

FIG. 4b shows a schematic side view of the depiction in FIG. 4a.

FIG. 4c shows a schematic cross-section along the line Ivc-Ivc according to FIG. 4a.

FIG. 5b shows a schematic side view of the drawing in FIG. 5a.

FIG. 5c shows a schematic cross-section along the line Vc-Vc as in FIG. 5a.

FIG. 6b shows an enlarged section along the line Vib-Vib, as in FIG. 6a.

Figure 1:
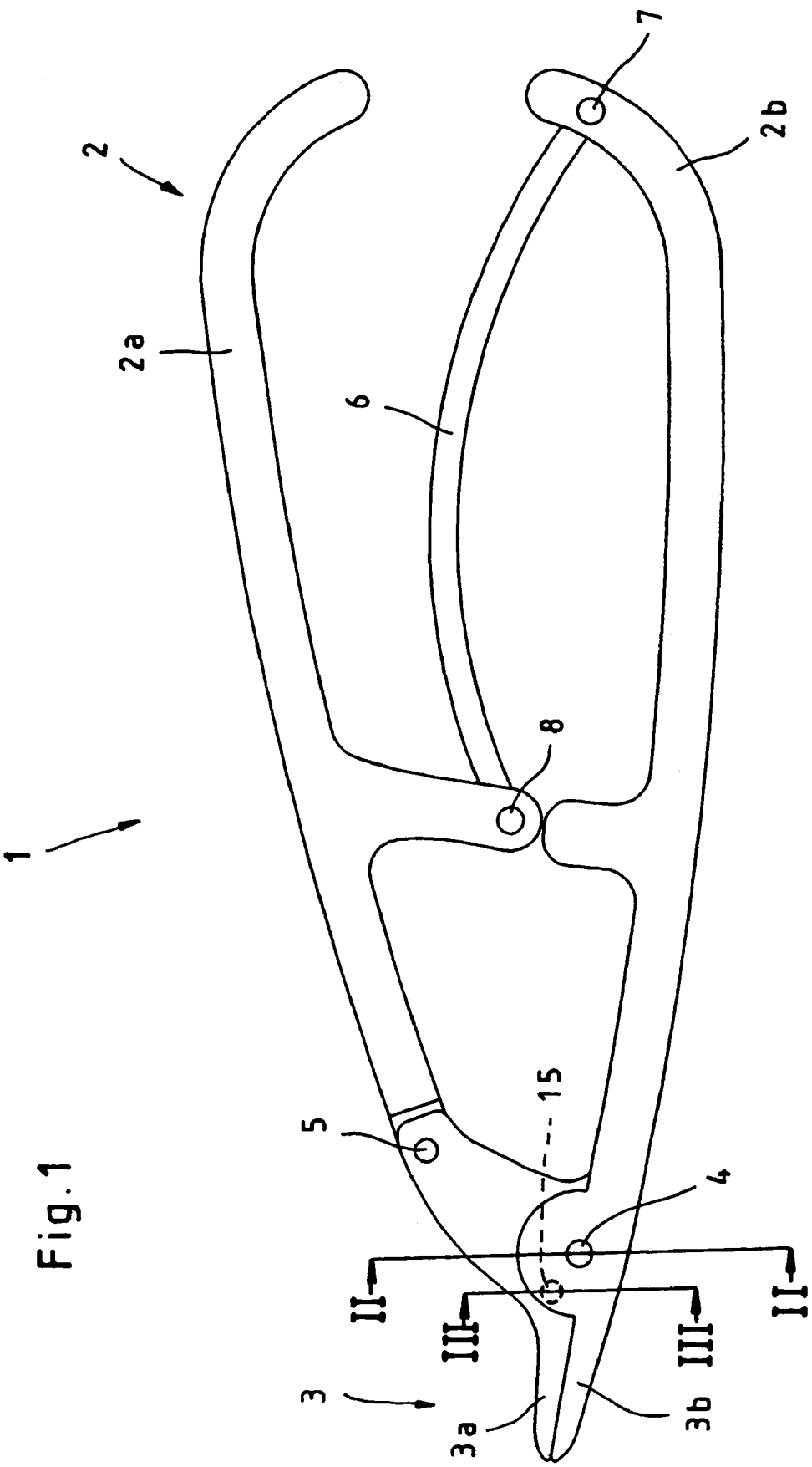
FIG. 1 shows a schematic side view of a first embodiment of an inventive gripping and/or retaining instrument.

The medical gripping and/or retaining instrument illustrated in FIG. 1a is a surgical needle holder 1.

The needle holder 1, of pincer-like form, consists essentially of a proximal handle 2 with two handgrips 2a and 2b as well as a distal side retaining part 3 with two jaw members 3a and 3b, which can rotate relative to one another around a swivel axis 4.

In the first embodiment of the needle holder 1, illustrated in FIG. 1, the handgrip 2b and the jaw member 3b are connected with one another rigidly to form a single unit, whereas the other handgrip 2a and the other jaw member 3a are rotatably connected to one another by a hinge point 5. In this illustrated embodiment, the jaw members 3a, 3b and the handgrips 2a, 2b do not cross one another.

As can further be seen from FIG. 1, a guide element configured as a leaf spring is positioned between the handgrips 2a and 2b of the handle 2, and this guide element is mounted with one end on a retaining point 7 in the area of the proximal end of the rigid handgrip 2b and with the other end on a mounting point 8 in the central area of the rotatable handgrip 2a. The leaf spring 6 serves to fix the handgrips 2a, 2b or the jaw members 3a, 3b of the retaining part 3 in defined end positions, namely in an open end position of the retaining part 3 and in a closed end position of the retaining part 3.

The retaining part 3 of the needle holder 1 contacts a needle 9 to be held between jaw members 3a, 3b by means of gripping surfaces 10, as can be seen from FIGS. 4b, 4c, and 5b, 5c. In the illustrated embodiment, the gripping surface 10 of the lower jaw member 3b is level in configuration and the gripping surface 10 of the upper jaw member 3a is configured as vaulted inward in the longitudinal direction of the jaw member 3a.

As is shown in the sectional illustrations of FIGS. 2a to 3b, the upper jaw member 3a is mounted so that it can rotate with respect to the lower jaw member 3b around the longitudinal axis of this jaw member 3a. This rotatable mounting in the direction of the arrow V in the illustrated embodiment is accomplished by the fact that the lower jaw member 3b has two parallel side walls 11 set apart from one another for receiving the swivel axis 4, and the upper jaw member 3a is mounted on the swivel axis 4 by means of a stud 12 between the two parallel side walls 11 and at a distance to both side walls 11, and thus the stud 12 forming the mounting hub is configured to taper on both sides in the area of the mounting on the swivel axis 4, as is made clear in FIGS. 2a and 2b.

Because of the tapering on the stud 12, there is an essentially linear mounting of the stud 12 on a surrounding circular course on the swivel axis 4, so that the upper jaw member 3a can rotate to right or left because of the lateral distance between the stud 12 and the side walls 11 of the lower jaw member 3b, as viewed in the longitudinal direction of the jaw member 3a.

Figure 5A:
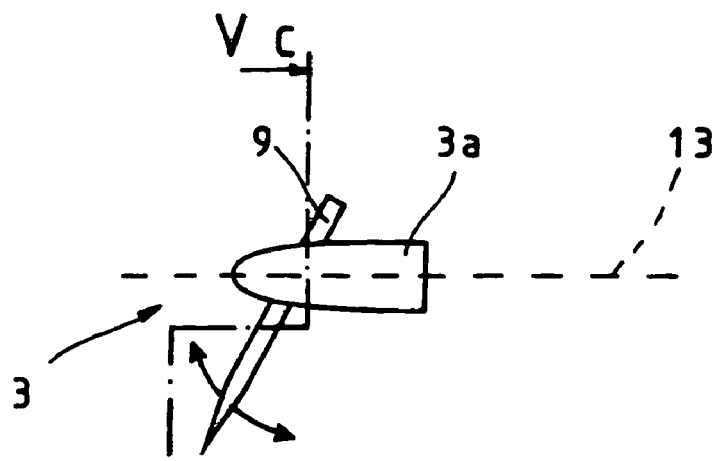
FIG. 5a shows a schematic overhead view of a retaining part of an inventive gripping and/or retaining instrument with a needle held between the jaw members not at a right angle to the instrument's axis.
Figure 5B:
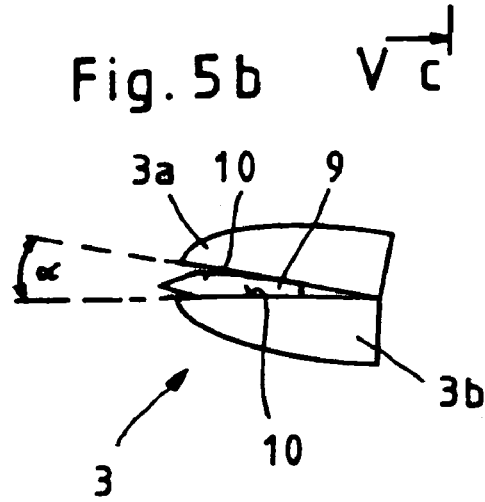
Figure 5C:
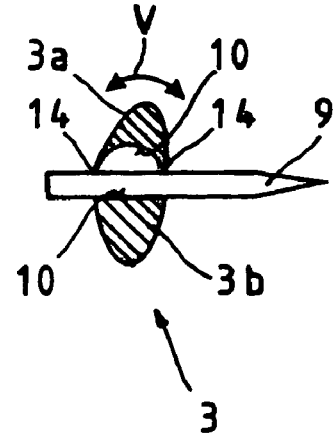

As is shown from a comparison of FIGS. 4c and 5c, this rotatable mounting of the upper jaw member 3a is necessary if the needle 9 positioned between the jaw members 3a, 3b is also to be secured against rotation and held stable when the needle is not positioned between the gripping surfaces 10 of the jaw members 3a, 3b at a right angle to the instrument's longitudinal axis 13.

In FIGS. 4a to 4c the needle 9 is positioned at a right angle to the instrument's longitudinal axis 13 between the jaw members 3a and 3b. Because of the cylindrical shaft of the needle 9 with an essentially unchanging diameter, the needle 9 is positioned in the right-angle posture with its entire surface on the level gripping surface 10 of the lower jaw member 3b and is contacted by two contact points 14 of the gripping surface 10 of the upper jaw member 3a. This linear contact on the lower jaw member 3b together with the two-part placement on the upper jaw member 3a causes a rotation-resistant mounting of the needle 9 in the retaining part 3.

Because the distance between the jaw members 3a, 3b of the retaining part 3 in each selected opening angle increases (with increasing distancing from the swivel axis 4), it is not possible to grasp a needle 9 that is not positioned at a right angle to the instrument's longitudinal axis 13 by means of the gripping surfaces 10 of the jaw members 3a, 3b, so that it is rotation-resistant if the jaw members 3a, 3b are mounted to be rotatable exclusively around the swivel axis 4 but are otherwise mounted rigidly.

As soon as the needle 9 is not positioned at a right angle to the instrument's longitudinal axis 13 between the jaw members 3a, 3b, the opening angle alpha formed between the jaw members 3a, 3b causes the closing jaw members 3a, 3b to grip the needle 9 by clamping exclusively with the areas of the gripping surfaces 10 that are situated closest to the swivel axis 4, so that only a punctual contact is possible between the gripping surfaces 10 and the needle 9. However, this merely punctual mounting of the needle 9 between the jaw members 3a, 3b is very unstable, with the result that a needle 9 held in such a manner can rotate relative to the instrument's longitudinal axis 13 at the slightest pressure.

The rotatable mounting of the upper jaw member 3a, however, allows the gripping surfaces 10 of the upper jaw member 3a, by means of rotation, to adjust to the varying distances between the jaw members 3a, 3b and again to grip the needle 9 in such manner that the upper jaw member 3a grips the needle 9 on two contact points 14 set apart from one another and presses them to form an essentially linear-shaped contact on the gripping surface 10 of the lower jaw member 3b, as can be seen in FIG. 5c. This linear contact on the lower jaw member 3b together with the two-point mounting on the upper jaw member 3a causes, again, a rotation-resistant mounting of the needle 9 in the retaining part 3.

As the sectional sketches of FIGS. 3a and 3b also show, the stud 12 of the upper jaw member 3a has a rod 15 secured in the stud 12, running perpendicular to the instrument's longitudinal axis 13, and this rod 15 is mounted in the side walls 11 of the lower jaw member 3b and is configured preferably to be rounded at its ends. This rod 15, which is mounted in the side walls 11 so that it can be tipped, is intended to prevent relative motion of the upper jaw member 3a in the direction of the instrument's longitudinal axis 13 toward the lower jaw member 3b.

To prevent rotation of the jaw member 3a from simultaneously also causing rotation of the handgrip 2a connected with this jaw member 3a, it is possible to configure the mounting of the jaw member 3a on the handgrip 2a in the area of the axis of the hinge point 5 so that it is similar to the mounting on the swivel axis 4 in such a way that the mounting allows the components 2a, 3a to tip toward one another. The hub that makes this tipping possible can be configured either on the jaw member 3a or on the handgrip 2a.

This tippable mounting between handgrip 2a and jaw member 3a, together with the guide element positioned between the handgrips and configured as a leaf spring, makes possible a stable and non-tippable motion of the handgrip 2a of the handle 2, because this mounting in the area of the hinge point 5 compensates in turn for the possible rotation of the jaw member 3a.

Figure 6A:
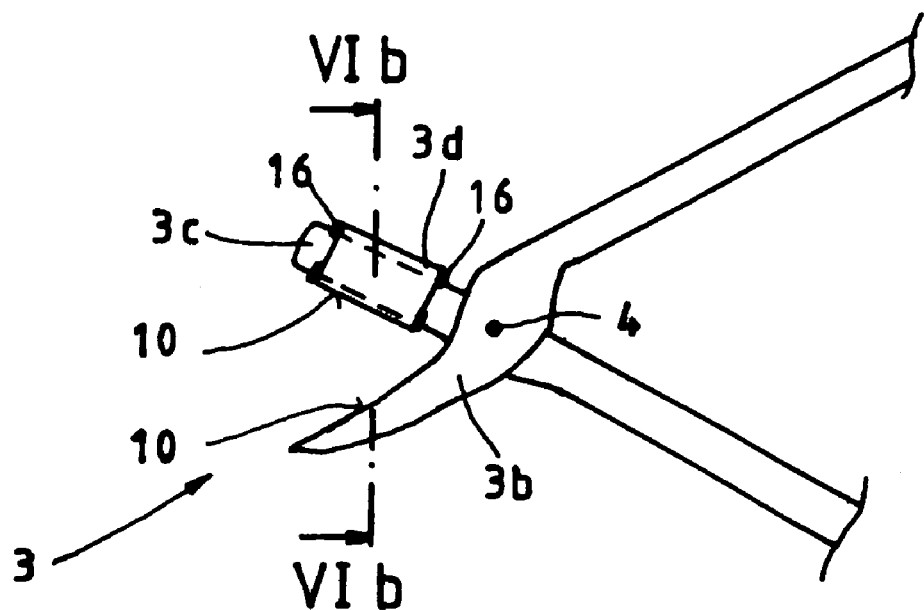
FIG. 6a shows a partial schematic side view of a second embodiment of an inventive medical gripping and/or retaining instrument.
Figure 6B:
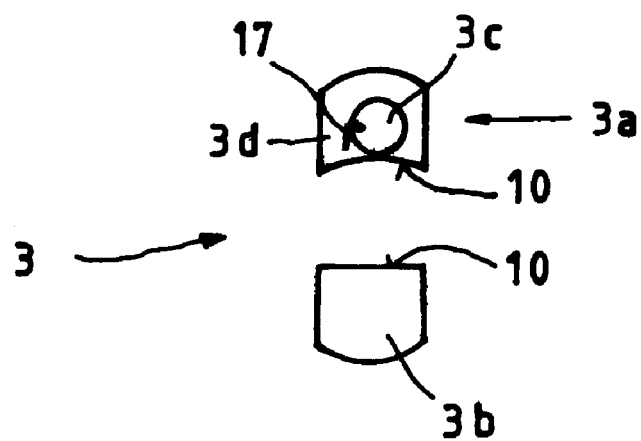

In the second embodiment, illustrated in FIGS. 6a and 6b, the jaw member 3a has a two-part structure consisting of an essentially rigid part 3c and a part 3d that is mounted on the rigid part 3c and can rotate around its longitudinal axis. As shown in FIG. 6a, the rotatable part 3d is fixed to the rigid part 3c in the longitudinal direction of the rigid part 3c by securing elements 16, for instance securing rings and/or form-matching mountings.

To facilitate handling of this kind of jaw member 3a, mountings can be provided to restrict the rotation angle of the rotatable part 3d, so that the gripping surface 10 of the rotatable part 3d is always positioned essentially facing toward the gripping surface 10 of the other jaw member 3b.

This restriction of the rotation angle of the rotatable part 3d, in FIG. 6b, is accomplished by a spring element 17 that is positioned between the rigid part 3c and the rotatable part 3d and which in addition pre-stresses the rotatable part 3d into the starting position shown in FIG. 6b.

The embodiment shown in FIGS. 6a and 6b is distinguished in that the rotation of the rotatable part 3d of the jaw member 3a cannot cause any tipping of the handgrip 2a.

Figure 7:
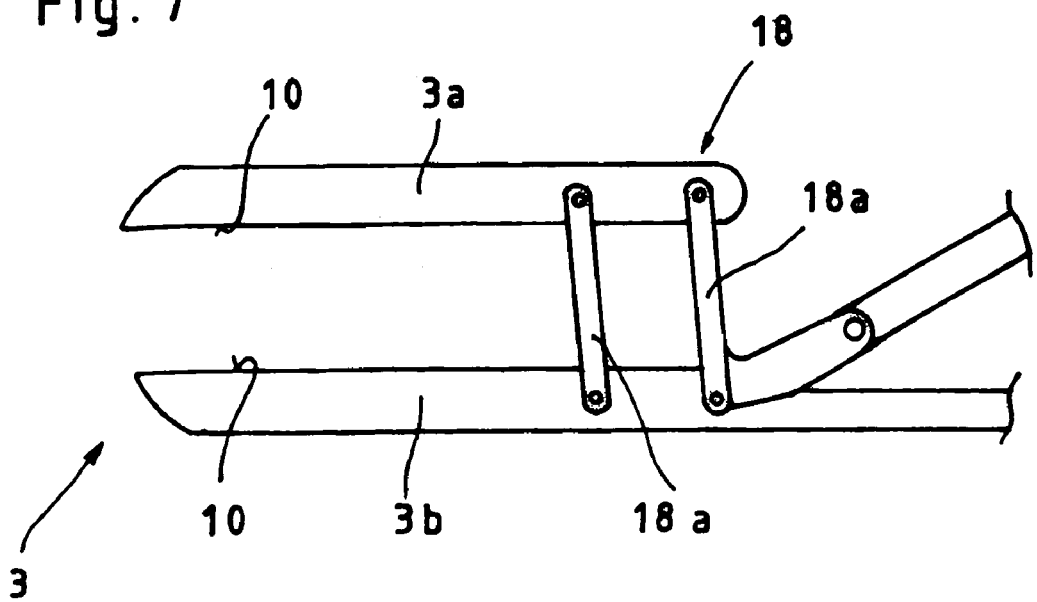
FIG. 7 shows a partial schematic side view of a third embodiment of an inventive medical gripping and/or retaining instrument.

In the third embodiment of the needle holder, shown in FIG. 7, the jaw member 3a is mounted so that it can be displaced relative to jaw member 3b in the direction of the longitudinal axis of the jaw member 3a. This rotatable property of jaw member 3a ensures that the gripping surfaces 10 of the jaw members 3a and 3b are situated at all times essentially parallel to one another, so that a gripped object is always held so that it cannot rotate. To achieve this parallel mounting of the jaw member 3a, in the illustrated embodiment, a parallelogram rod structure is provided which consists of two gears 18a.

In the embodiment illustrated in FIG. 7, it is also possible to configure at least one jaw member 3a or 3b of the retaining part 3 in such a way that, as shown in FIGS. 6a and 6b, in a medical gripping and/or retaining instrument configured in this way, at least one jaw member 3a or 3b can be displaced in to planes in order to grip firmly and to prevent rotation of an object held between the jaw members 3a and 3b.

KEY TO THE ILLUSTRATIONS 1 needle holder
2 handle
2a handgrip
2b handgrip
3 retaining part
3a jaw member 3b jaw member
3c rigid part
3d rotatable part
4 swivel axis
5 hinge point
6 leaf spring
7 mounting point
8 mounting point
9 needle
10 gripping surface
11 side wall
12 stud
13 instrument's longitudinal axis
14 contact point
15 rod
16 securing elements
17 spring element
18 parallelogram rod structure
18a gear
V tippability
alpha opening angle

What is claimed is:

1. A medical gripping and/or retaining instrument comprising
 a handle comprising two handgrips; and
 a retaining part comprising two jaw members capable of activation by the handle, wherein the jaw members can be rotated with respect to one another about a swivel axis; and
 distinguished in that the first jaw member, to receive the swivel axis, has two parallel side walls set apart from one another and the second jaw member is configured in the area between the two parallel side walls as a stud, which is mounted at a distance from both walls on the common swivel axis in such a way that the second jaw member of the retaining part can rotate around its longitudinal axis; and
 wherein the stud forming a hub in the area of the mounting on the swivel axis has a bore hole, and the stud is configured so that the bore hole in the stud forming the hub tapers from both sides of the stud to the middle of the bore hole all the way to the outer diameter of the swivel axis.

2. A medical gripping and/or retaining instrument according to claim 1, distinguished in that the stud is mounted in essentially linear form on the swivel axis.

3. A medical gripping and/or retaining instrument according to claim 1, distinguished in that gripping surfaces of the jaw members are in contact with an object held between the jaw members of the retaining part independently of its angle position with respect to an instrument's longitudinal axis, in such a manner that the gripping surfaces each contact the object on at least two contact points at a distance from one another.

4. A medical gripping and/or retaining instrument according to claim 3, distinguished in that at least one gripping surface of a jaw member contacts the object in essentially linear form.

5. A medical gripping and/or retaining instrument according to claim 4, distinguished in that the gripping surface of one jaw member is of level configuration and the gripping surface of another jaw member working together with this jaw member, viewed in the longitudinal direction of this jaw member, is of vaulted configuration when viewed facing away from the contact surface with the object to be held.

6. A medical gripping and/or retaining instrument according to claim 5, distinguished in that a handgrip of the handle is configured to form one piece rigidly with a jaw member of the retaining part, while the other handgrip of the handle is connected with the other jaw member of the retaining part so that it can rotate around a hinge point, and that the handgrips are connected to one another by at least one guide element, in particular a leaf spring, and the guide element is mounted with one end on a mounting point in the area of the proximal end of the one handgrip and with the other end on a mounting point in the middle area of the other handgrip.

7. A medical gripping and/or retaining instrument according to claim 6, distinguished in that the rotatable handgrip or the rotatable jaw member is mounted on the hinge axis of the hinge point so that it is tippable with respect to the respective other component.

8. A medical gripping and/or retaining instrument according to claim 7, characterized by a rod secured in the stud of the one jaw member, running perpendicular to the instrument's longitudinal axis and mounted in the side walls of the other jaw member.

9. A medical gripping and/or retaining instrument according to claim 8, distinguished in that the rod is mounted in the side walls so that it can be tipped around the instrument's longitudinal axis.

* * * * *